United States Patent [19]

Weinstein et al.

[11] Patent Number: 5,213,561
[45] Date of Patent: May 25, 1993

[54] METHOD AND DEVICES FOR PREVENTING RESTENOSIS AFTER ANGIOPLASTY

[76] Inventors: Joseph S. Weinstein, 200 Wagner Pl. #906, Memphis, Tenn. 38103; H. Frank Martin, 5108 Greenway Cove, Memphis, Tenn. 38117

[21] Appl. No.: 855,445

[22] Filed: Mar. 19, 1992

Related U.S. Application Data

[63] Continuation of Ser. No. 577,916, Sep. 6, 1990, abandoned.

[51] Int. Cl.⁵ ............................................ A61M 36/12
[52] U.S. Cl. .................................... 600/7; 600/3; 128/657
[58] Field of Search ............... 606/108, 155, 191, 192, 606/194, 195, 198; 604/95; 128/898, 657, 770; 600/3, 7, 8

[56] References Cited

U.S. PATENT DOCUMENTS

| | | | |
|---|---|---|---|
| 3,674,006 | 7/1972 | Holmer | 600/7 |
| 3,866,050 | 2/1975 | Whitfield | 378/64 |
| 4,819,618 | 4/1989 | Liprie | 600/7 |
| 4,851,694 | 7/1989 | Rague et al. | 600/3 |
| 4,963,128 | 10/1990 | Daniel et al. | 600/7 |
| 4,976,680 | 12/1990 | Hayman et al. | 600/7 |
| 5,059,166 | 10/1991 | Fischell et al. | 600/3 |

FOREIGN PATENT DOCUMENTS

0012004  6/1980  European Pat. Off. ............... 600/7

OTHER PUBLICATIONS

Advanced Cardiovascular Systems, Inc. brochure "Hartzler ACX ™ Coronary Dilatation Catheter".
Scimed ™, GSSC 0.018 Skinny ™ PTCA Dilatation Catheter Instructions for use.

*Primary Examiner*—C. Fred Rosenbaum
*Assistant Examiner*—Wm. Lewis
*Attorney, Agent, or Firm*—Wood, Herron & Evans

[57] ABSTRACT

The incidence of restenosis after angioplasty is reduced by exposing the potentially stenotic site to radiation from a source within the same vascular structure in which the site is located. The radioactive source can be mounted at the distal end of a guidewire, or in a balloon catheter, or on a balloon expansible stent, and is inserted through the vascular structure to the site to be exposed.

12 Claims, 1 Drawing Sheet

METHOD AND DEVICES FOR PREVENTING RESTENOSIS AFTER ANGIOPLASTY

This application is a continuation, of U.S. patent application Ser. No. 577,916, filed Sep. 6, 1990 now abandoned.

FIELD OF THE INVENTION

This invention relates to the treatment of stenotic sites after angioplasty, for the purpose of reducing restenosis, and to a surgical method and apparatus for such treatment.

BACKGROUND OF THE INVENTION

Percutaneous transluminal coronary angioplasty ("PTCA") is an established treatment for coronary artery disease. The procedure involves inserting a balloon catheter through a vascular structure to a structure site at which atherosclerotic plaque has collected on the vessel wall. (As used herein the term "vascular structure" includes arteries, veins and the coronary structures which carry blood.) The plaque is disrupted by inflating the balloon at the distal end of the catheter, thereby increasing the intraluminal diameter of the vascular structure and spreading or loosening the plaque. Disruption of the plaque ultimately reduces the restriction to the blood flow through the vascular structure. After sufficient expansion, the balloon is then collapsed and removed, and the area of disruption heals.

While the PCTA procedure is very widely used, one problem which limits its acceptability is a condition known as restenosis.

Restenosis is the development of further blockage in the intravascular structure, following otherwise successful PTCA at the angioplasty site. Restenosis is believed to be an exaggerated form of a normal healing process following the stretching; it occurs in approximately 20–50 percent of cases.

Restenosis is thought to be caused by fibrointimal proliferation of the stretched wall in which the injured cells lining the vascular structure multiply and form fibrous tissue. Fibrointimal proliferation at the vascular wall is an almost malignant phenomenon in which normal cells multiply at a high rate, thereby creating an obstruction to flow through the vascular structure.

Various techniques and devices have been proposed to deal with the problem of restenosis. These include laser, atherectomy, radio frequency and ultrasound treatments and the use of expandable stents. To date, no device has eliminated the problem of restenosis.

SUMMARY OF THE INVENTION

This invention utilizes radiation treatment from within the vascular structure to reduce the incidence of restenosis. Radiation therapy has been successful to treat a variety of cancers, in which abnormal cells proliferate at a high rate, but so far as we are aware, radiation treatment from within the vascular structure to lessen restenosis has never been proposed. In accordance with the method of this invention, the intravascular site on which the angioplasty was performed is exposed to radiation from within the vessel in which the site is located. The radiation source is inserted through the vascular structure to the site by an elongated flexible member, in a manner which may be similar to or coincidental with the manner in which the balloon catheter is inserted. The radiation exposure may be a relatively brief single dosage from a relatively high intensity source such as Cobalt 60, following which the radiation source is removed through the vascular structure. Alternatively, in another method of the invention, a radioactive source of lower intensity and having a half life correlated to the expected development period of a restenosis, is inserted and left at the site for a longer exposure. Restenosis typically occurs during the first six months following angioplasty; Iridium 192 has a half life of 74 days, so that it is uniquely suited for this latter purpose, because it becomes largely ineffective and innocuous after the typical period of occurrence of restenosis. In this case the source is left indefinitely in the vascular structure.

Several different devices can be used to carry out the method of the invention. Three specific devices are disclosed, including a radiation guidewire, a radiation balloon, and a balloon expandable radioactive stent.

The radiation guidewire is an elongated, flexible wire suitable for longitudinal insertion through the vascular structure to the site of the angioplasty. The wire itself may be of the conventional type used in angioplasty, for example such as that sold by Advanced Cardiovascular Systems, Inc. under the designation "Hi-Torque Floppy." The radiation source, for instance Cobalt 60, is attached to or coated on the distal end of the guidewire. The radiation source is preferably shielded with a movable shielding, such that it is effectively covered during insertion and withdrawal. Once the source has been positioned at the angioplasty site, the shielding, which may be in the form of an axially shiftable sleeve around the wire, is shifted longitudinally to expose the radioactive source.

In the second embodiment of the invention, the radioactive material is placed on the catheter tube inside the balloon of a balloon catheter. A retractable sleeve having a lead or lead coated distal end surrounds the source.

The third embodiment includes an expansible stent around the balloon of a balloon catheter wherein the stent is made of, or has applied to it, a less intense radioactive source such as Iridium 192. The stent, which can be of wire mesh, is expansible within the vascular structure by expansion of the balloon. Once the stent has been expanded, the balloon is collapsed and withdrawn from within the stent; the stent remains at the site as its radioactivity diminishes.

The range of effective radiation dosage has not yet been determined but is believed to correlate with the dosages used in the treatment of cancerous tumors by implanted radioactive seeds. For example, it is believed that 20 cGy.(0.2 Rad.) could be effective in certain cases, but this has not been experimentally verified. The duration of exposure will of course vary inversely with the intensity of the radiation source; higher intensity sources require shorter exposures and vice versa. As used herein, the term "dosage" and "exposure" is intended to mean and refer to such intensity and duration as is preselected for reducing the incidence of restenosis in the particular situation.

DESCRIPTION OF THE DRAWINGS

The invention can best be described by reference to the accompanying drawings showing various devices in accordance with the invention, in which.

DETAILED DESCRIPTION OF THE INVENTION

Figure 1:
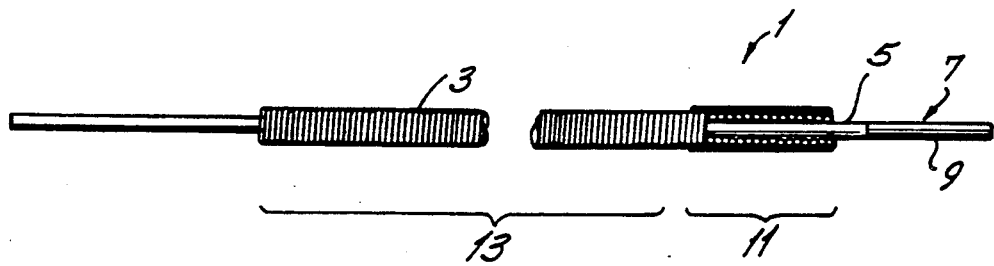
FIG. 1 is a longitudinal section of a guidewire having a radioactive tip, in accordance with a first embodiment.

FIG. 1 of the drawings shows a balloon catheter guidewire 1 which can be inserted through the center of a balloon catheter for steering the catheter through vascular structure to a site where an angioplasty is to be performed. The guidewire 1 has an outer sleeve 3 around an inner or center wire 5. The guidewire structure 1 is sized to fit within a balloon catheter tube to allow guidance or steering of the balloon catheter by manipulation of guidewire 1. The outer sleeve 3 of the guidewire is preferably a tightly wound wire spiral or coil of stainless steel, with an inside diameter large enough so that it can be slid or shifted longitudinally with respect to the inner wire 5. The distal end 7 of inner wire 5 is the portion of the guidewire 1 which is to be positioned for radiation treatment of the site of the angioplasty. The distal end 7 has a radioactive material 9 such as Cobalt-60 which provides an intravascular radiation source, that is, it can be inserted through the vascular structure and will irradiate the site from within, as distinguished from an external radiation source. Outer sleeve 3 has an end portion 11 at its distal end which is made of or coated with a radiation shielding substance for shielding the radioactive source 9. In a preferred embodiment, the shielding section is lead or lead coated steel. The remaining portion 13 of the outer sleeve 3, extending from shielding section 11 to the other end of guidewire 1 (opposite from distal end 7) can be of a non-shielding substance such as stainless steel wire. By way of example, the guidewire may for example be 150 cm. long with an 0.010" inner wire, having a 30 mm. long radioactive end 9, and a sleeve 3 of 0.018" diameter having a lead coating 11 which is 30 cm. long. Except for the radioactive source 9 and retractable shielding 11 at the tip, guidewire 1 may be generally conventional.

As already noted, the outer sleeve 3 of the guidewire 1 is slidable over the inner wire 5, at least for a distance sufficient to cover and uncover radioactive material 9, so that the shielding section 11 of the outer sleeve can be moved away from the radioactive material 9 to expose the angioplasty site to radiation. After the exposure, the outer sleeve is shifted again to cover the radioactive section. Such selective shielding prevents exposure of the walls of the vascular structure when the guidewire 1 is being inserted or removed.

Figure 2:
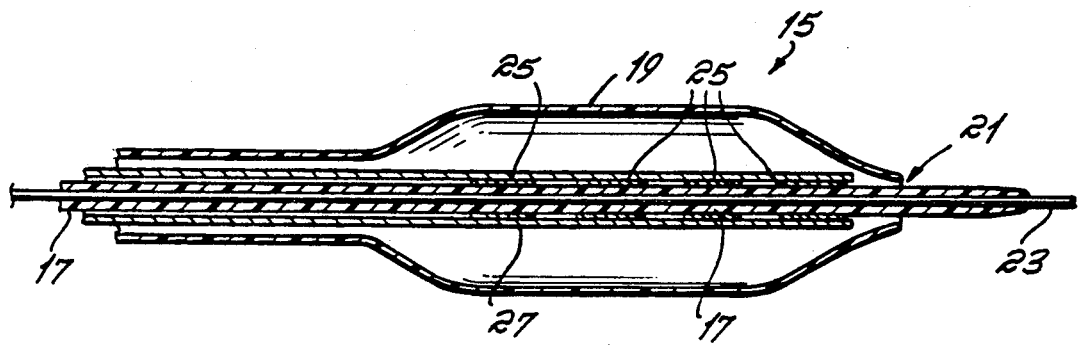
FIG. 2 is a diagrammatic longitudinal section of a radiation balloon catheter in accordance with a second embodiment of the invention.

A second embodiment of the invention, as shown in FIG. 2, includes a balloon catheter 15. The balloon catheter 15 has a balloon 19 at its distal end 21 and is constructed of a medically suitable plastic, preferably polyethylene. Catheter 15 has a center core or tube 17 in which a conventional guidewire 23 is receivable. Particles or crystals of radioactive material 25 (which again may be Cobalt-60) are embedded in or mounted on tube 17 inside balloon 19. A retractable radiation shielding sleeve 27 is slidable along tube 17 and covers source 25, blocking exposure to radiation, until it is shifted away (to the left in FIG. 2). Upon completion of angioplasty, the shielding sleeve 27 is retracted and the area of the injury is irradiated. Such structure allows radiation of the vascular structure immediately following completion of angioplasty, without separately inserting a radiation source.

Figure 3:
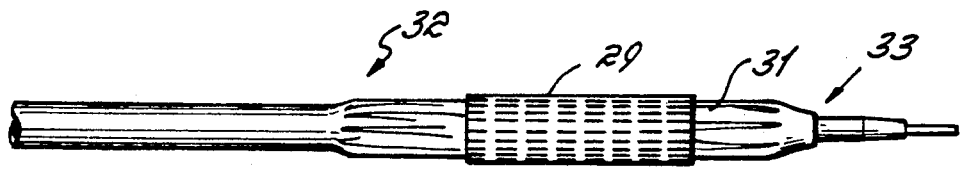
FIG. 3 is a diagrammatic longitudinal view of a balloon expandable radioactive stent in accordance with a third embodiment.
Figure 4:
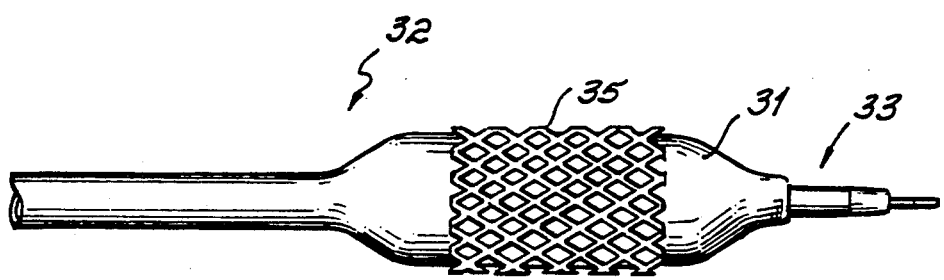
FIG. 4 is a view similar to FIG. 3, but shows the stent when it has been expanded by the balloon.

A third embodiment of the invention, shown in FIGS. 3 and 4, incorporates a balloon mounted stent 29 made of a radioactive material. Stent 29 can be in the form of an expandable wire or mesh cage and is mounted over the balloon portion 31 at substantially the distal end 33 of the balloon catheter 32. The stent is made of or coated with a radioactive material such as Iridium 192 which will remain effectively radioactive just for 4-5 months, a period sufficient to reduce restenosis which typically occurs in the first six months following angioplasty. Stent 29 is expanded by inflation of the balloon portion 31, as shown in FIG. 4. After the balloon portion 31 has been deflated, catheter 32 can be removed from the site of the angioplasty. The expanded stent 35 remains at the site of the angioplasty. Balloon expandable stents are already known, but not with a radioactive material associated with them.

From the foregoing it can be appreciated that the invention provides devices and methods which can be incorporated and used in a well known and tested method for treatment of coronary artery and related diseases.

While the present invention has been illustrated by a description of the preferred embodiments which have been described in detail, it is not the intention of the applicants to restrict or in any way limit the scope of the appended claims to such detail. Additional advantages and modifications will readily appear to those skilled in the art. For example, radiation elements can otherwise be attached within the balloon catheter structure or on a guidewire in accordance with the scope of the following claims.

What is claimed is:

1. A device for reducing the incidence of restenosis at a site within a vascular structure following percutaneous transluminal coronary or peripheral angioplasty of said site, comprising, an elongated flexible member which is insertable longitudinally through vascular structure, an intravascular radioactive source mounted at a distal end of said flexible member, said source being positionable at an intravascular angioplasty site within said vascular structure for radiating said site by inserting said flexible member longitudinally through said structure, radiation shielding means on said flexible member for selectively shielding and exposing said radioactive source, said shielding means being a retractable sleeve around said radioactive source, said sleeve being selectively movable relative to said source to expose said source when said source has been positioned at said site, thereby to radiate said site, said flexible member, source and shielding means having dimensions sufficiently small that said device is insertable longitudinally through said vascular structure.

2. The device of claim 1 wherein said flexible member is a guidewire, said sleeve and radioactive source being mounted on and movable with said guidewire for withdrawal from said vascular structure.

3. The device of claim 1 wherein said flexible member is a guidewire.

4. The device of claim 3 wherein said guidewire comprises an outer sleeve around an inner wire.

5. The device of claim 4 wherein said radioactive source is mounted to a distal end of said inner wire.

6. The device of claim 1 wherein said radioactive source is Cobalt 60.

7. A device for reducing the incidence of restenosis at a site within a vascular structure following percutaneous transluminal coronary or peripheral angioplasty of said site, comprising,
- an elongated flexible member which is insertable longitudinally through vascular structure,
- an intravascular radioactive source mounted at a distal end of said flexible member,
- said source being positionable at an intravascular angioplasty site within said vascular structure for radiating said site by inserting said flexible member longitudinally through said structure,
- radiation shielding means on said flexible member for selectively shielding and exposing said radioactive source,
- said shielding means being a retractable sleeve around said radioactive source, said sleeve being in the form of a coil having a radiation shielding coating, said sleeve being selectively axially shiftable relative to said source to expose said source when said source has been positioned at said site, thereby to radiate said site.

8. The device of claim 7 wherein said coating is a lead coating on a wire coil.

9. A device for reducing the incidence of restenosis at a site within a vascular structure following percutaneous transluminal coronary of peripheral angioplasty of said site, comprising,
- an elongated flexible member which is insertable longitudinally through vascular structure,
- an intravascular radioactive source mounted at a distal end of said flexible member,
- said source being positionable at an intravascular angioplasty site within said vascular structure for radiating said site by inserting said flexible member longitudinally through said structure,
- radiation shielding means on said flexible member for selectively shielding and exposing said radioactive source,
- said shielding means being a retractable sleeve around said radioactive source, said sleeve being selectively movable relative to said source to expose said source when said source has been positioned at said site, thereby to radiate said site,
- said flexible member being guidewire which extends axially through a balloon catheter.

10. A device for reducing the incidence of restenosis at a site within a vascular structure following percutaneous transluminal coronary or peripheral angioplasty of said site, comprising,
- an elongated flexible member which is insertable longitudinally through vascular structure,
- an intravascular radioactive source mounted at a distal end of said flexible member,
- said source being positionable at an intravascular angioplasty site within said vascular structure for radiating said site by inserting said flexible member longitudinally through said structure,
- radiation shielding means on said flexible member for selectively shielding and exposing said radioactive source,
- said shielding means being a retractable sleeve around said radioactive source, said sleeve being selectively movable relative to said source to expose said source when said source has been positioned at said site, thereby to radiate said site,
- said flexible member being a guidewire which comprises an outer sleeve around an inner wire, said sleeve comprising a wire coil.

11. A device for reducing the incidence of restenosis at a site within a vascular structure following percutaneous transluminal coronary or peripheral angioplasty of said site, comprising,
- an elongated flexible member which is insertable longitudinally through vascular structure, said flexible member being a plastic tube of a catheter having a balloon at one end thereof,
- an intravascular radioactive source mounted at a distal end of said flexible member,
- said source being positionable at an intravascular angioplasty site within said vascular structure for radiating said site by inserting said flexible member longitudinally through said structure, said radioactive source being mounted to the distal end of said tube, inside said balloon.
- radiation shielding means on said flexible member for selectively shielding and exposing said radioactive source,
- said shielding means being a retractable sleeve around said radioactive source, said sleeve being selectively movable relative to said source to expose said source when said source has been positioned at said site, thereby to radiate said site.

12. The device of claim 1 further including a shiftable sleeve around said tube, said sleeve having a shield for selectively exposing said source.

* * * * *